US006653282B1

(12) United States Patent
Benedict et al.

(10) Patent No.: US 6,653,282 B1
(45) Date of Patent: Nov. 25, 2003

(54) PEPTIDE COMPOSITIONS WHICH INDUCE IMMUNE TOLERANCE AND METHODS OF USE

(76) Inventors: Stephen H. Benedict, Dept. of Microbiology Univ. KS, Lawrence, KS (US) 66045; Teruna J. Siaiiann, 2912 Iris La., Lawrence, KS (US) 66047; Marcia A. Chan, Dept. Molecular Bioscience, Univ. Kansas, Lawrence, KS (US) 66045; Scott A. Tibbetts, 5636 Waterman Blvd., Apt. 33, St. Louis, MO (US) 63112

( * ) Notice: Subject to any disclaimer, the term of this patent is extended or adjusted under 35 U.S.C. 154(b) by 0 days.

(21) Appl. No.: 09/479,378

(22) Filed: Jan. 5, 2000

Related U.S. Application Data

(62) Division of application No. 08/844,978, filed on Apr. 23, 1997, now Pat. No. 6,075,004
(60) Provisional application No. 60/057,848, filed on Apr. 26, 1996.

(51) Int. Cl.$^7$ .................. A61K 38/00; A61K 39/395
(52) U.S. Cl. ................ 514/12; 514/2; 424/130.1
(58) Field of Search .................. 424/130.1; 514/2, 514/12

(56) References Cited

U.S. PATENT DOCUMENTS

| 5,340,800 A | 8/1994 | Liu et al. |
| 5,437,958 A | 8/1995 | Gallatin et al. |
| 5,470,953 A | 11/1995 | Gallatin et al. |

FOREIGN PATENT DOCUMENTS

| EP | 0391088 | 10/1990 |
| EP | 0362526 | 6/1995 |
| WO | 9118010 | 11/1991 |
| WO | 9118011 | 11/1991 |

OTHER PUBLICATIONS

Meyer et al (J. Immunol 1995 Oct. 1;155(7):3578–84).*
Stanley et al (EMBO J 1994 Apr. 15;13(8):1790–8).*
Isobe et al (Science 1992 Feb. 28;255(5048):1125–7).*
Cierniewski et al (Eur J Biochem 1988 Oct. 15;177(1):109–115).*
Chirathaworn et al.: Cross–linking of ICAM–1 on T cells induces transient tyrosine phosphorylation and inactivation of cdc2 kinase; *The Journal of Immunology*; 155:5479–5482 (1995).
Dustin et al.; T–cell receptor cross–linking transiently stimulates adhesiveness through LFA–1; *Nature*; 341:619–624 (1989).
Butler et al.; Modulation of T cell morphology and induction of homotypic adhesion by a protein tyrosine kinase inhibitor; *Cellular Immun.*, 162:1–10 (1995).
Pierschbacher et al.; Synthetic peptide with cell attachment activity of fibronectin; *Proc. Natl. Acad. Sci. USA*; 80:1224–1227 (1983).
Pierschbacher et al.; Call attachment activity of fibronectin can be duplicated by small synthetic fragments of the molecule; *Nature*, Macmillan Journals Ltd., 1984.
Randi et al.; I domain of $\beta_2$ integrin lymphocyte function-–associated antigen–1 contains a binding site for ligand intercellular adhesion molecule–1; *J. Biol. Chem.*, 269(17):12395–12396 (1994).
Nortamo et al.; A peptide from ICAM–2 binds to the leukocyte integrin CD11a/CD18 and inhibits endothelial cell adhesion; *J. Biol. Chem.*, 268(23):17513–17518 (1993).
Ross et al.; Inhibition of molt–4–endothelial adherence by synthetic peptides from the sequence of ICAM–1; *J. Biol. Chem.*, 267(12):8537–8543 (1992).
Masumoto et al.; Multiple activation states of VLA–4; *J. Biol. Chem.*; 268(1):228–234 (1993).
Stanley et al.; Integrin LFA–1 $\alpha$ subunit contains an ICAM–1 binding site in domains V and VI; *EMBO J.*; 13(8):1790–1798 (1994).
*Current Protocols in Immunology*, vol. 1, Sections. 4.4.1–4.4.12 (1992), Green Publishing Associates, Inc. and John Wiley & sons, Inc.
Flory, Phase changes in proteins and polypeptides; *Mellon Institute*, Pittsburg, PA (date unknown).
Merrifield; The chemical synthesis of peptides and proteins; Rockefeller University, New York, NY; Copyright 1971 by Beckman Instruments, Inc.
van Kooyk et al.; Activation ofLFA–1 through a $Ca^{2+}$ –dependent epitope stimulates lymphocyte adhesion; *J. Cell Biology*; 112(2):345–354 (1991).
Welder et al.; Inhibition of cell adhesion by microspheres coated with recombinant soluble intercellular adhesion molecule–$1^1$; *J. Immunology*; 150(6):2203–2210 (1993).
Isobe et al.; Specific acceptance of cardiac allograft after treatment with antibodies to ICAM–1 and LFA–1; *Science*; 255:1125–127 (1992).
Springer; Adhesion receptors of the immune system; *Nature*; 346:425–433(1990).
Tuomanen; Subversion of leikocyte adhesion systems by respiratory pathogens; *ASM News*; 59(6):292–296 (1993).
Sherman–Gold; Companies pursue therapies based on complex cell adhesion molecules; *Genetic Engineering News*; 13(13):6 (1993).

(List continued on next page.)

*Primary Examiner*—Anthony C. Caputa
*Assistant Examiner*—Christopher Yaen
(74) *Attorney, Agent, or Firm*—John R. Wetherell, Jr.

(57) ABSTRACT

Peptide compositions which inhibit the binding of one protein to another protein, and corresponding methods of use are disclosed. These peptide compositions include at least one peptide which binds to one protein, and at least one peptide which binds to the other protein. In the preferred embodiment, the peptide composition is composed of a combination of cyclic ICAM-1-based and LFA-1-based peptides which inhibit the binding of LFA-1 to ICAM-1. Such LFA-1/ICAM-1-based peptide compositions can be used to treat disease states such as rejection of transplanted organs, allergies, and autoimmune diseases.

17 Claims, 12 Drawing Sheets

OTHER PUBLICATIONS

Waldmann et al.; the use of monoclonal antibodies to achieve immunological tolerance; *Immunology Today*; 14(6):247–251 (1993).

Steinman; Autoimmune disease; *Scientific American*; 107–114 (1993).

Marrack et al.; How the immune system recognizes the body; *Scientific American*; 81–89 (1993).

Weissman et al.; How the immune system develops; *Scientific American*; 65–71 (1993).

Nossal; Life, death and the immune system; *Scientific American*; 53–62 (1993).

Nakakura et al.; Potent and effective prolongation by anti–LFA–1 monoclonal antibody monotherapy of non–primarily vascularized heart allograft survival in mice without T cell depletion; *Transplantation*; 55(2):412–417 (1993).

Talento et al.; A single administration of LFA-1 antibody confers prolonged allograft survival; *Transplantation*; 55(2):418–422 (1993).

Ezzell; Anitbody combo nixes graft rejection; *Science News*; vol. 14 (date unknown).

Merrifield; Automated synthesis of peptides; *Science*; 15:178–185 (1965).

Larson et al.; Primary structure of the leukocyte function–associated molecule–1 α subunit: anintegrin with an embedded domain defining a protein superfamily; *J. Cell Biology*; 108:703–712 (1989).

Landis et al.; A novel LFA–activation epitope maps to the I domain; *J. Cell Biology*; 120(6):1519–1527 (1993).

Li et al.; A leukocyte integrin binding peptide from intercellular adhesion molecule–2 stimulates T cell adhesion and natural killer cell activity; *J. Biol. Chem.*; 268(29):21474–21477 (1993).

The Adhesion Molecule Facts Book, Pigott & Power, Academic Press (San Diego), 1993, pp. 93–97, 74–78.

Hynes; Integrins: Versatility, Modulation and Signaling in Cell Adhesion; *Cell*; 69:11–25 (1992).

* cited by examiner

US 6,653,282 B1

PEPTIDE COMPOSITIONS WHICH INDUCE IMMUNE TOLERANCE AND METHODS OF USE

RELATED APPLICATION

This application is a divisional (and claims the benefit of priority under 35 USC 120) of U.S. application Ser. No. 08/844,978, filed Apr. 23, 1997 now U.S. Pat. No. 6,075,004, which claims priority to Provisional Application No. 60/057,848, filed Apr. 26, 1996. The disclosure of the prior applications are considered part of (and are incorporated by reference in) the disclosure of this application.

SEQUENCE LISTING

A printed Sequence Listing accompanies this application, and also has been submitted with identical contents in the form of a computer-readable ASCII file on a floppy diskette.

BACKGROUND OF THE INVENTION

1. Field of the Invention

The present invention is broadly concerned with compositions of two or more peptides effective in inhibiting the binding of proteins, and corresponding methods of use. More particularly, the preferred form of the invention relates to peptide compositions which inhibit the binding of leukocyte function-associated antigen (LFA-1) and intercellular adhesion molecule (ICAM-1); these peptide compositions can be used to treat disease states such as rejection of transplanted organs, allergies, and autoimmune diseases.

2. Description of the Prior Art

Many biological phenomena involve the mutual recognition of proteins. For example, it has been known for decades that antibodies bind to antigens in order to protect the body against foreign substances (Carayannopoulos et al., 1993, Imnunoglobulins, Structure and Function, In: Fundamental Immunology, Paul, W. E., Ed., pp. 283–314, Raven Press). Also, Ras and Raf-1 are proto-oncoproteins that transduce growth and differentiation signals initiated: by tyrosine kinases; ras binds to Raf-1 and thereby inhibits Ras-GAP activity (Zhang et al., 1993, *nature* 364:308–313). Yeast Cdc7 protein kinase and Dbf protein are both required for the initiation of DNA replication; these proteins bind to each other, and it is thought that Dbf4 is specific for the activation of Cdc7 kinase (Jackson et al., 1993, *Mol. Cell Biol.* 13:2899–2908). Yeast GAL4 protein consists of two protein subunits which, when bound together, activate the genes encoding enzymes of galactose utilization (Fields et al., 1989, *Nature* 340:245–246).

It is also widely known that the contact sites within proteins that bind to one another are noncontinuous domains of amino acids. These contact sites can be found in different subunits of a protein as in the case of the heavy and light chains of antibodies (Carayannopoulos et al., 1993; Perutz, 1992, Protein Structure, New Approaches to Disease and Therapy, pp. 41–76, W. H. Freeman and Co.). Alternatively, these contact sites can be found in different areas of the same subunit as in the case of the α subunit of LFA-1 (Edwards et al., 1995, *J Biol Chem.* 270:12635–12640; Stanley et al., 1994, *EMBO* 13: 1790–1798).

Many autoimmune diseases occur when T-cells of an organism recognize and react to "self" proteins. This recognition occurs when specific proteins on the surface of the T-cells bind to the corresponding self proteins. This type of reaction results in rheumatoid arthritis, insulin-dependent diabetes mellitus, and multiple sclerosis. Allograft rejection also results from T-cell attack.

Initiation of an immune response to an antigen involves interaction of a small subset of T-cells with the antigen, followed by activation and proliferation of those T-cell clones. Complete T-cell activation requires two signals: (1) interaction of the T-cell receptor with an appropriate MHC-antigen complex, and (2) a second signal provided by adhesion molecules. The second signal may be provided by binding of the adhesion receptor, LFA-1 (CD 11a and CD 18), to one of its counter-receptors such as ICAM-1 (CD54) (Staunton et al., 1990, *Cell* 61:243–254). If the second signal is blocked, the antigen-specific T-cells are induced to die by apoptosis or to enter a state of cellular anergy. Blockage of this interaction by monoclonal antibodies to LFA-1 and ICAM-1 results in increased survival time for mice receiving heart allografts (Isobe et al., 1992, *Science* 255:1125–1127).

Previous studies have shown that peptide fragments from ICAM-1 can inhibit T-cell-endothelial adherence (Ross et al., 1992, *J Biol. Chem.* 267:8537–8543), HIV-1 replication in MT-2 cells (Fecondo et al., 1993 *Aids Research and Human Retroviruses* 9:733–740), homotypic adhesion of Raji cells, and cytotoxic cell-mediated killing of K562 cells. Peptides from the sequence of the α subunit of LFA-1 have also been shown to inhibit binding of T-cells to ICAM-1 (Stanley et al., 1994, *EMBO* 13:1790–1798). Additionally, short-chain peptides derived from active sites of ICAM-1 and LFA-1 also inhibit these types of interactions (Benedict et al., 1995, International Publication No. WO 95/28170, the teachings of which are incorporated by reference herein). However, there are no reports in the prior art of peptide compositions which are effective in inducing immune tolerance in an organism.

SUMMARY OF THE INVENTION

The present invention is predicated upon the idea that compositions of short-chain peptides can inhibit the binding of one protein (a first protein) to another protein (a second protein). The mutual binding of a pair of proteins is responsible for signal transductions occurring in many biological processes. In the case of the immune response, inhibition of such protein binding can result in induction of immune tolerance. Therefore, the peptide compositions of the present invention can be used, for example, as a treatment for disease states such as rejection of transplanted organs, allergies, and autoimmune diseases (e.g., rheumatoid arthritis, insulin-dependent diabetes mellitus, and multiple sclerosis).

Specifically, the present invention is directed to peptide compositions, and methods of using these compositions, wherein at least one peptide binds to the first protein, and at least one peptide binds to the second protein, whereby the first protein is inhibited from binding to the second protein. Preferably, the first protein is an integrin (e.g., the α and β subunits of LFA-1) while the second protein is an integrin-binding protein (e.g., ICAM-1).

If the protein system is the LFA-1/ICAM-1 system, each peptide which binds to LFA-1 is derived from ICAM-1, while each peptide which binds to ICAM-1 is derived from LFA-1. Ideally, each ICAM-1-based peptide contains a sequence present in a sequence selected from the group consisting of Sequence ID Nos. 1–14, contains a sequence selected from the group consisting of Sequence ID Nos. 1–14, or has a sequence selected from the group consisting of Sequence ID Nos. 1–14; furthermore, each LFA-1-based peptide contains a sequence present in a sequence selected from the group consisting of Sequence ID Nos. 15–35, contains a sequence selected from the group consisting of Sequence ID Nos. 15–35, or has a sequence selected from the group consisting of Sequence ID Nos. 11–35.

Advantageously, each peptide is not immunogenic, and has a molecular weight under 20 kilodaltons. Preferably, each peptide contains at least one unnatural amino acid (i.e., an amino acid that is itself not of the 20 normally found amino acids, or one of the normal 20 amino acids in an abnormal location) and is cyclic in order to protect the peptide from degradation. Although the peptides described herein for the purposes of illustration are separate molecules, the present invention comprehends use of peptides which are attached to one another. In the most preferred embodiment of the invention, the peptide composition includes a combination of cyclic peptides (e.g., peptides having the sequences of Sequence ID Nos. 7, 19, 26, and 34).

DETAILED DESCRIPTION OF THE PREFERRED EMBODIMENT

Figure 1:
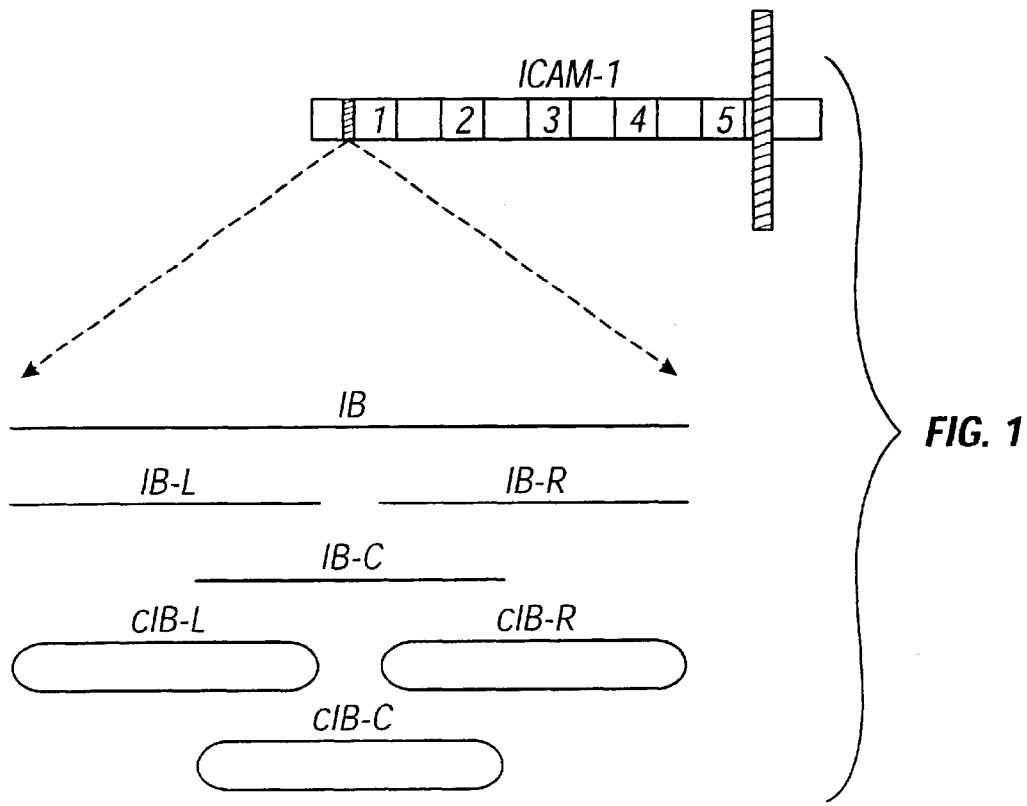
FIG. 1 is a diagram illustrating ICAM-1-based peptides IB, IB-L, IB-C, IB-R, cIB-L, cIB-C, and cIB-R, and the locations in ICAM-1 from which their sequences were derived (see footnote 1 of the table below for peptide nomenclature)

The present invention is directed to compositions containing two or more peptides which inhibit the binding of a first protein to a second protein. Specifically, at least one peptide binds to the first protein, and at least one peptide binds to the second protein. In general terms, these peptide compositions are made according to the following steps:

1. A protein system is selected in which a first protein binds to a second protein.

2. The contact sites within the proteins are identified.

3. Peptides having sequences found within the contact sites are synthesized.

4. The peptides are assayed to determine which peptides inhibit binding of the two proteins.

5. Combinations of peptides containing at least one first protein-binding peptide (derived from the second protein) and at least one second protein-binding peptide (derived from the first protein) are assayed to determine which combinations are effective in inhibiting the binding of the two proteins.

6. The peptides and compositions are assayed in biological assay, e.g., a mixed lymphocyte reaction, induced arthritis study and/or skin transplant study.

In regard to step 1, the prior art abounds with examples of protein systems in which a first protein binds to a second protein. A few of these examples are described above.

In regard to step 2, there are three standard methods by which contact sites within proteins are identified. All three methods require that the gene encoding the protein is cloned and sequenced. Hundreds of such gene sequences have been reported in the prior art. If the gene encoding the protein of interest has not been cloned and sequenced, the state of molecular biology today makes clear that doing so is routine to a skilled artisan.

These three methods are summarized as follows:

a. The first method has been previously described (Stanley et al., 1994, *EMBO* 13:1790–1798, the teachings of which are incorporated by reference herein). In this method, a domain of the first or second protein is removed by deleting the corresponding segment from the gene encoding the protein. The altered gene is expressed in bacteria to produce an altered protein. The altered protein is then assayed for its ability to bind to the other protein. If the altered protein does not bind to the other protein, the contact site was removed. The contact site is thereby localized.

b. The second method is employed once a contact site has been localized as described above. This method involves site-directed mutagenesis of the gene of the protein to identify precisely which amino acids are involved in protein binding. A specific nucleotide is changed in order to change a single amino acid in the contact site. An altered protein generated in this manner is then assayed for its ability to bind to the other protein as described above. The importance of the specific amino acid to protein binding is thereby deduced. Those skilled in the art recognize that site-directed mutagenesis is a routine and widely-used technique. In fact, many site-directed mutagenesis kits are commercially available. One such kit is the "Transformer Site Directed Mutagenesis Kit" sold by Clontech Laboratories (Palo Alto. Calif.).

c. The third method is the "Yeast Two-Hybrid System." This method can be performed using commercially available kits. One such kit is the "MATCHMAKER Two-Hybrid System" sold by Clontech Laboratories (Palo Alto, Calif.). In this method, a domain of the first protein is subcloned into a plasmid (Plasmid A) and is expressed in yeast as a fusion protein. This fusion protein contains a domain of a yeast transcription factor in addition to the domain of the first protein. The gene of the second protein is also subcloned into a plasmid (Plasmid B) and is also expressed in yeast as a fusion protein; in this case, the fusion protein contains a different domain of the yeast transcription factor. If the domains of the first protein and the second protein bind within the yeast cell, a functional hybrid transcription factor is formed from the transcription-factor domains encoded by Plasmids A and B. This hybrid transcription factor results in the expression of a reporter gene. Thus, expression of the reporter gene indicates that the domains of the first and second proteins contain contact sites of Proteins A and B.

In regard to step 3, those skilled in the art would recognize that peptides can be commercially synthesized by a variety of laboratories.

In regard to step 4, Example 1 below gives a detailed protocol for conducting a homotypic-adhesion assay. This assay can be used to determine which peptides inhibit the binding of LFA-1 to ICAM-1 if the LFA-1/ICAM-1 system was selected in step 1. If a different protein system was selected, an antibody-binding assay can be used to carry out step 4. This assay, as applied to the LFA-1/ICAM-1 system, is described in Benedict et al., *Modulation of T Cell Morphology and Induction of Homotypic Adhesion by a Protein Tyrosine Kinase Inhibitor*, Cellular Immunology, 162:001–010 (1995), incorporated by reference herein. However, those skilled in the art would understand that the antibody-binding assay can be used with other protein systems, and would know how to modify the assay accordingly.

In regard to step 5, combinations of peptides can be assayed as described in step 4, except that multiple peptides are tested simultaneously rather than a single peptide.

In regard to step 6, the examples below give details of mixed lymphocyte reaction (MLR), rheumatoid arthritis (RA) and skin graft studies. MLR is the normally best predictor of in vivo activity to aid in selection of inhibiting peptides. This is because the MLR measures a biological readout, namely cell interaction followed by induced proliferation. Thus, the MLR is a direct measurement of allogeneic T cell responses. Moreover, the MLR directly models the events involved in bone marrow transplantation, and indirectly predicts the biological effectiveness of the peptides in solid organ transplantation and in the treatment of autoimmune diseases such as rheumatoid arthritis, insulin-dependent diabetes and multiple sclerosis. A detailed protocol of the MLR is set forth in Example 4 below.

The protein system selected by the applicants to illustrate the preferred embodiment of the invention was the LFA1/ICAM-1 system. Noncontiguous domains of LFA-1 and ICAM-1 which were believed to be the contact sites of the two proteins were selected. The sequences of LFA-1 and ICAM-1 are known. Peptides based upon the sequences found in these contact sites were commercially synthesized using standard techniques. Some of the peptides were cyclized. Homotypic-adhesion assays using the peptides were conducted to determine which LFA-1-based peptides and which ICAM-1-based peptides inhibited the binding of LFA-1 to ICAM-1.

Five linear peptides (three LFA-1-based peptides and two ICAM-1-based peptides) that were individually effective in inhibiting protein binding were cyclized and combined. This combination was tested for its ability to inhibit the binding of LFA-1 to ICAM-1 using the homotypic-adhesion assay. Other peptides are constructed which individually and/or in combination inhibit the binding of LFA-1 and ICAM-1. These peptides and peptide combinations are injected into mice that have received skin allografts in order to determine which peptides or peptide combinations are effective in inhibiting the rejection of transplanted organs. Those of ordinary skill in the art understand that the results of in vitro and in vivo experiments described herein are predictive of the efficacy of such peptides and peptide combinations in inhibiting rejection of transplanted organs in humans and ameliorating autoimmune diseases.

EXAMPLE 1

The following examples are set forth by way of illustration only, and nothing therein shall be taken as a limitation upon the overall scope of the invention.

MATERIALS AND METHODS

Peptides. Peptides were synthesized either at the La Jolla Cancer Research Foundation (La Jolla, Calif.) or the University of Kansas, Department of Pharmaceutical Chemistry (Lawrence, Kans.). Peptide synthesis was generally conducted according to the standard-phase protocols employing t-butyloxycarbamate amino acid chemistry as previously described (Atherton et al., 1989, Solid Phase Peptide Synthesis: A Practical Approach, I.R.L. Press). Linear peptides having a penicillamine residue (Xaa in the Sequence Listing) or a cysteine residue at their amino-terminal ends and a cysteine residue at their carboxy-terminal ends were cyclized by forming a disulfide bridge between the terminal residues by adding dropwise a 2% aqueous potassium ferricyanide solution to dilute peptide solutions.

Homotypic-Adhesion Assay. Fresh human tonsils were suspended in TC-PBS containing 5% FCS and were minced. Cells in suspension were separated from tissue with a strainer, and the resulting cell suspension was used for T-cell separation. T-cells were isolated from other cells using the commonly used E-rosette method (Chirathaworn et al., 1995, *J. Immunol.* 155:5479–5482, the teachings of which are incorporated by reference herein). Cells were counted and resuspended in RPMI 1640 growth medium containing 5% FCS (hereafter referred to as RPMI) at $4 \times 10^6$ cells/ml and rested overnight at 37° C. Typically, greater than 98% of the purified cells were positive for the T-cell surface marker CD3, as assessed by flow cytometry.

96-well Falcon tissue culture plates were used for the homotypic-adhesion assay. pH neutralized, lyophilized peptides were resuspended in RPMI at a concentration of 5 mM. Aliquots of the peptides were added to each well at appropriate volumes to yield a final concentration of 1, 10, 100, 250, 500, or 1000 $\mu$M in a total sample volume of 100 $\mu$L. RPMI was added to each well to bring the total volume to 50 $\mu$L.

Freshly purified, resting cells were used for the assay. A quantity of cells sufficient for use in the assay was aliquoted from the stock. 50 $\mu$l of cell suspension was then added to each of the wells containing RPMI alone (unstimulated cells). To the remaining cells, PDB was added to a final concentration of $10^{-8}$ M. After mixing well, 50 $\mu$l of this cell suspension was added to each of the remaining wells. The plate was mixed gently, then incubated at 37° C. for 4 to 6 hours. After incubation, wells were photographed using an Olympus photomicroscope with a 40× magnification. Photographed samples were later assessed for index of clumping relative to the unstimulated and PDB-induced samples.

RESULTS

Peptides. The table below shows peptides constructed in accordance with the present invention, corresponding Sequence ID Numbers, and corresponding clumping-index values obtained from homotypic-adhesion assays:

| Peptide[1] | Sequence ID Number | Clumping Index[2] | n[3] |
|---|---|---|---|
| Control | | 0 ± 0 | 14 |
| PDB | | 100 ± 0 | 14 |
| IB[4] | 1 | 56 ± 7 | 14 |
| IB-L | 2 | 37 ± 26 | 4 |
| IB-C | 3 | 68 ± 12 | 6 |
| IB-R | 4 | ND[5] | — |
| cIB-L | 5 | 61 ± 9 | 7 |
| cIB-C | 6 | 61 ± 13 | 7 |
| cIB-R | 7 | 73 ± 8 | 6 |
| IE[6] | 8 | 63 ± 8 | 12 |
| IE-L | 9 | ND[5] | — |
| IE-C | 10 | 83 ± 3 | 2 |
| IE-R | 11 | ND | — |
| cIE-L | 12 | ND | — |
| cIE-C | 13 | 23 ± 3 | 2 |
| cIE-R | 14 | ND | — |
| LAB[7] | 15 | 75 ± 5 | 14 |
| LAB-L | 16 | 70 ± 10 | 6 |
| LAB-C | 17 | 77 ± 11 | 6 |
| LAB-R | 18 | ND | — |
| cLAB-L | 19 | 78 ± 13 | 5 |
| cLAB-C | 20 | 80 ± 15 | 3 |
| cLAB-R | 21 | 77 ± 11 | 6 |
| LAB.2[8] | 22 | 48 ± 10 | 6 |
| LAB.2-L | 23 | ND | — |
| LAB.2-C | 24 | 100 ± 0 | 3 |
| LAB.2-R | 25 | 100 ± 0 | 3 |
| cLAB.2-L | 26 | 50 ± 3 | 2 |
| cLAB.2-C | 27 | ND | — |
| cLAB.2-R | 28 | ND | — |
| LBE[9] | 29 | 73 ± 7 | 14 |
| LBE-L | 30 | 78 ± 5 | 6 |
| LBE-C | 31 | 62 ± 10 | 6 |
| LBE-R | 32 | 63 ± 9 | 7 |
| cLBE-L | 33 | 75 ± 10 | 6 |
| cLBE-C | 34 | 82 ± 7 | 5 |
| cLBE-R | 35 | 100 ± 0 | 2 |
| EBL[10] | 36 | 100 ± 0 | 5 |

Figure 2:
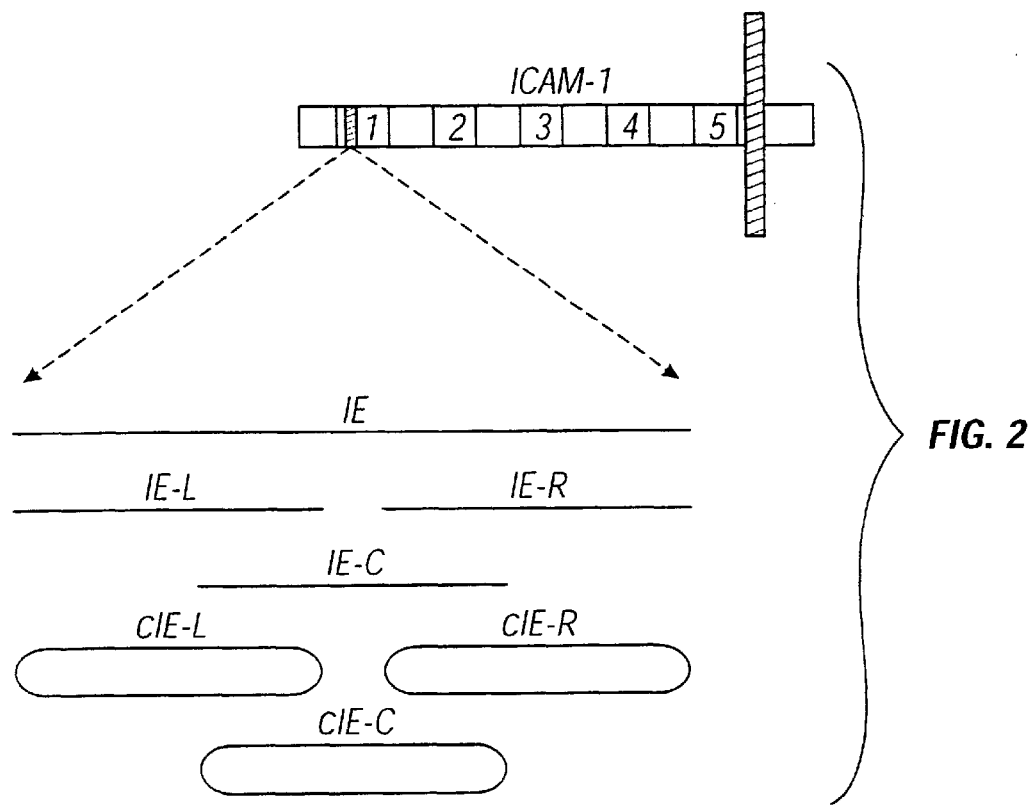
FIG. 2 is a diagram illustrating ICAM-1-based peptides IE, IE-L, IE-C, IE-R, cIE-L, cIE-C, and cIE-R, and the locations in ICAM-1 from which their sequences were derived.
Figure 3:
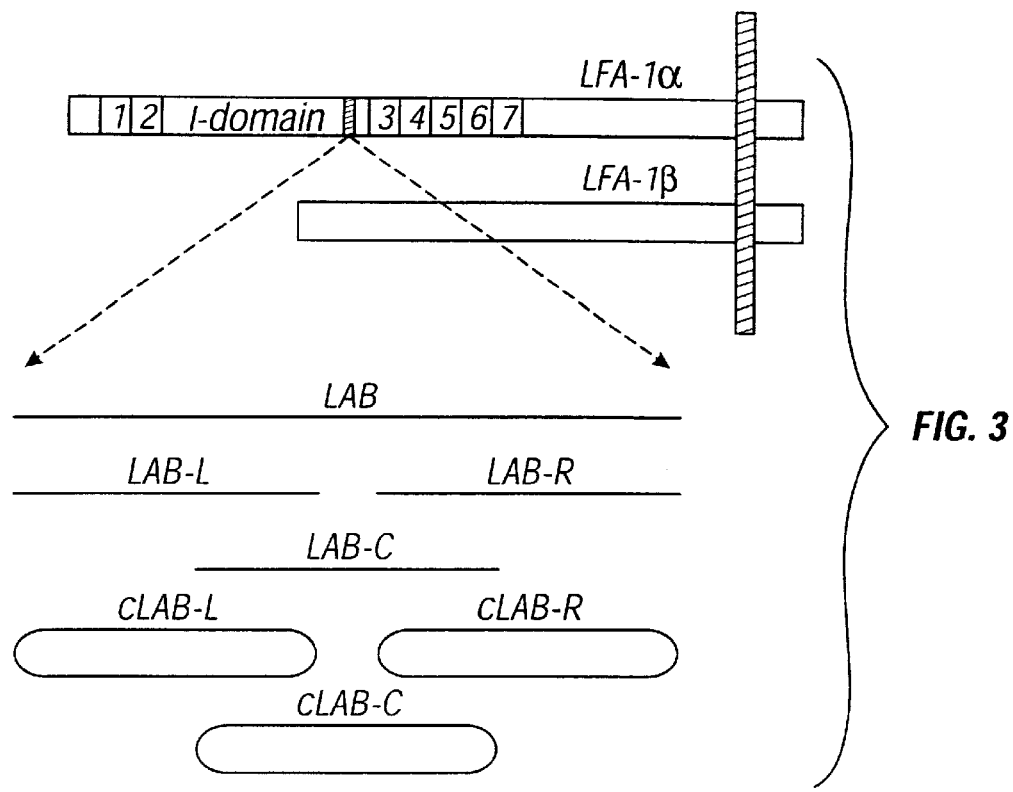
FIG. 3 is a diagram illustrating LFA-1 α-based peptides LAB, LAB-L, LAB-C, LAB-R, cLAB-L, cLAB-C, and cLAB-R, and the locations in the α subunit of LFA-1 from which their sequences were derived.
Figure 4:
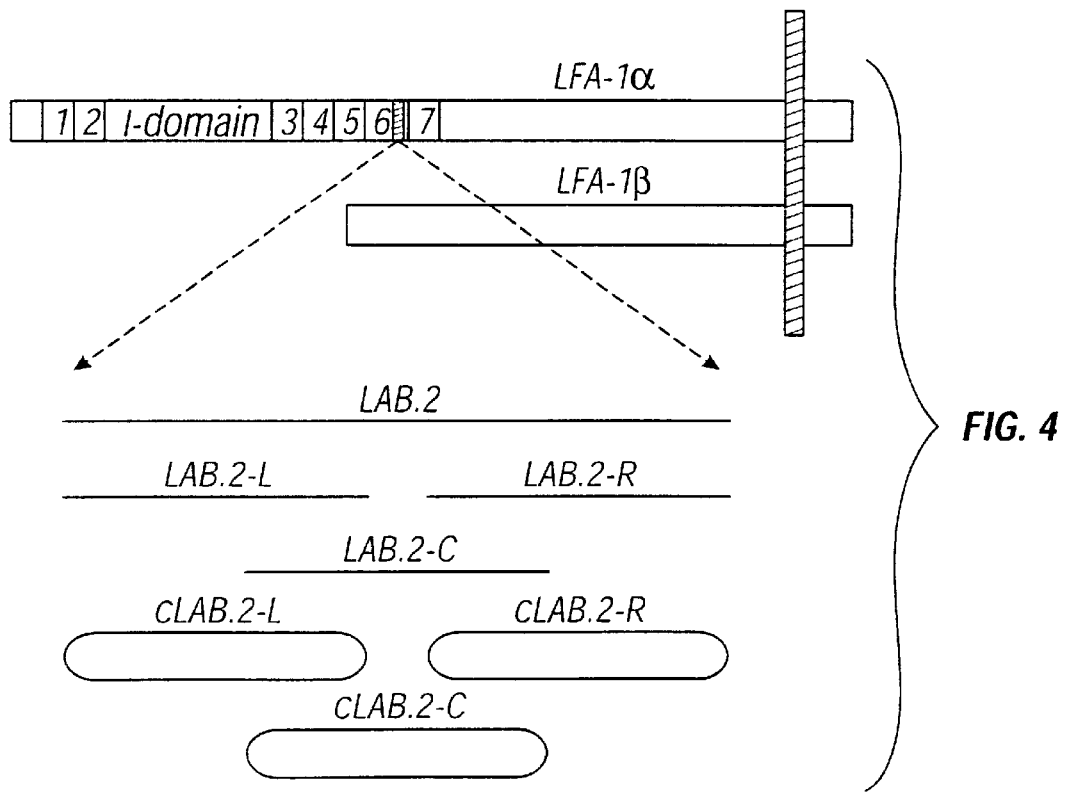
FIG. 4 is a diagram illustrating LFA-1α-based peptides LAB.2, LAB.2-L. LAB.2-C, LAB.2-R, cLAB.2-L, cLAB.2-C, and cLAB.2-R, and the locations in the a subunit of LFA-1 from which their sequences were derived.
Figure 5:
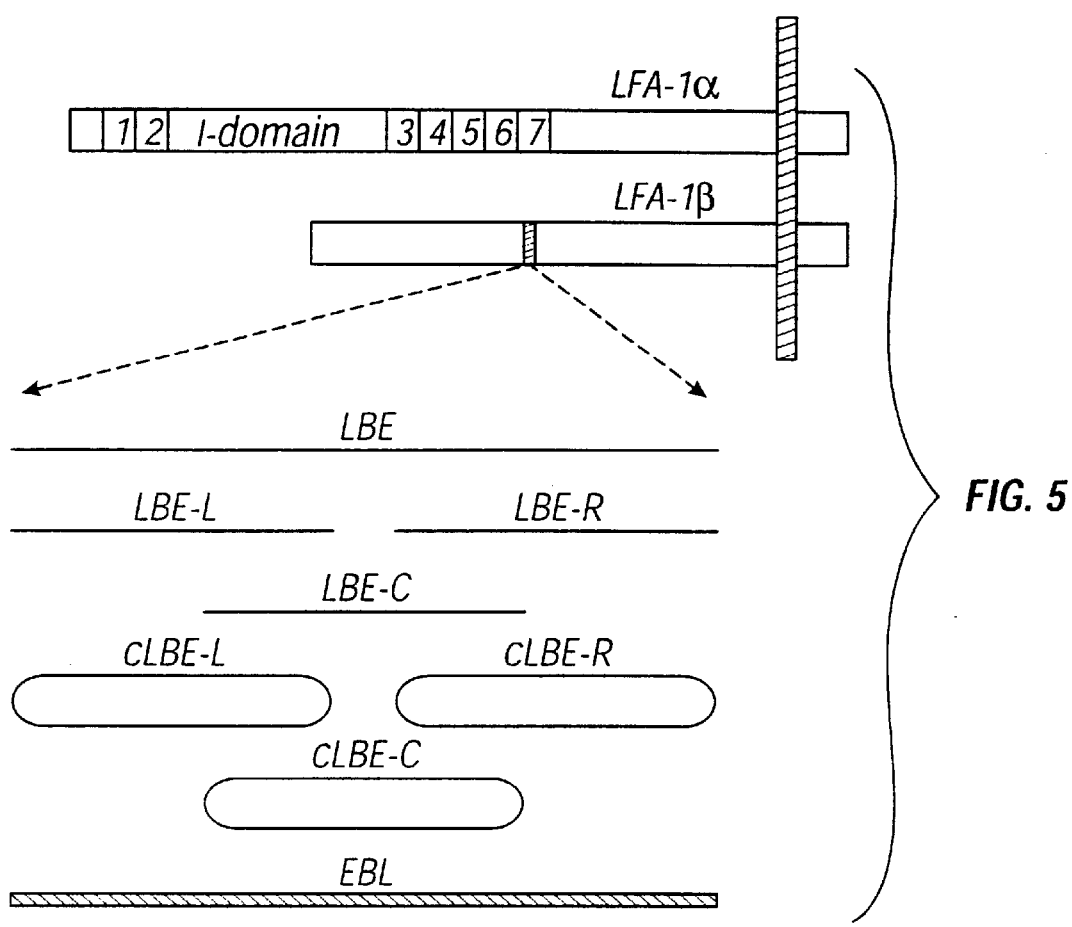
FIG. 5 is a diagram illustrating LFA-1β-based peptides LBE, LBE-L, LBE-C, LBE-R, cLBE-L, cLBE-C, and cLBE-R, and the locations in theβ subunit of LFA-1 from which their sequences were derived.

[1]Nomenclature of peptides is as follows: the first upper case letter indicates whether the peptide is derived from ICAM-1 (I) or LFA-1 (L); the second upper case letter in the name of each LFA-1 based peptide indicates whether the peptide is derived from the α (A) or β (B) subunit of LFA-1; the second upper case letter in the name of each ICAM-based peptide and the third upper case letter in the name of each LFA-1 based peptide indicates whether the peptide blocked (B) or enhanced (E) the binding of another peptide to either LFA-1 or ICAm-1 in previous studies; the upper case letter following a hyphen indicates whether the peptide is derived from the left (L), center (C), or right (R) segment of parent peptide IB, IE, LAB, LAB.2, or LBE; a lower case "c" indicates that the peptide is cyclic.
[2]The clumping index refers to the relative degree to which cells were clumped in the homotypic-adhesion assay; clumping-index values of 0 and 100 represent the mean clumping-index values of unstimulated cells and PDB-stimulated cells, respectively; the degree to which each peptide inhibited PDB-stimulated cell clumping is indicated by the magnitude of the respective clumping index; the closer the clumping index is to 0, the greater the degree of inhibition of cell clumping effected by the respective peptide. Clumping index was quantified by determining the mean clumping index per test run +/- standard error.
[3]Number of test runs.
[4]IB and peptides derived therefrom are illustrated in FIG. 1.
[5]Not done.
[6]IE and peptides derived therefrom are illustrated in FIG. 2.
[7]LAB and peptides derived therefrom are illustrated in FIG. 3.
[8]LAB.2 and peptides derived therefrom are illsutrated in FIG. 4.
[9]LBE and peptides derived therefrom are illustrated in FIG. 5.
[10]EBL, which has the reverse sequence of LBE and was used as a negative control, is illustrated in FIG. 5.

Homotypic-Adhesion Assay. The table above gives the results of the homotypic-adhesion assays using individual peptides. In this assay, PDB induces intercellular clumping of human T-cells by activating the LFA1/ICAM-1 binding interaction between the T-cells. Test runs which do not include PDB do not result in significant cell clumping, while test runs including only PDB result in maximal clumping.

The degree to which PDB-stimulated cell clumping is inhibited by a peptide indicates the degree to which the peptide blocks the interaction between LFA-1 present on the surface of one T-cell and ICAM-1 present on the surface of another T-cell. Those peptides which gave a clumping-index value of less than 100 all showed statistically significant inhibition of PDB-stimulated cell clumping, indicating that these peptides inhibit the binding of LFA-1 to ICAM-1. Significantly, cIE-C inhibited PDB-stimulated cell clumping to a much greater extent than its linear parent IE-C, suggesting that cyclic fragments of IE may inhibit the binding of LFA-1 to ICAM-1 to a greater extent than the parent peptide IE.

Figure 6:
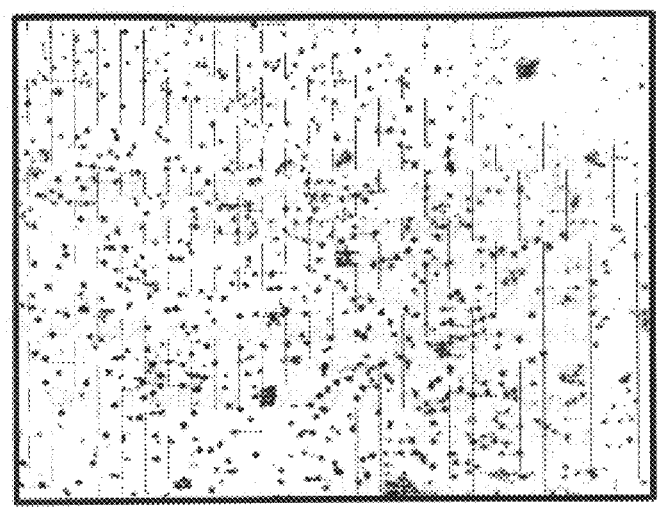
FIG. 6 is a photograph showing cells from a homotypic-adhesion assay wherein the cells were unstimulated.
Figure 7:
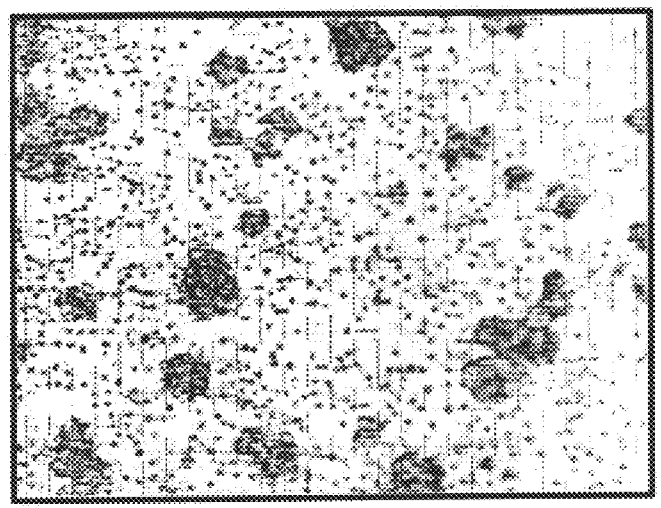
FIG. 7 is a photograph showing cells from a homotypic-adhesion assay wherein the cells were phorbol 12,13-dibutyrate (PDB)-stimulated.
Figure 8:
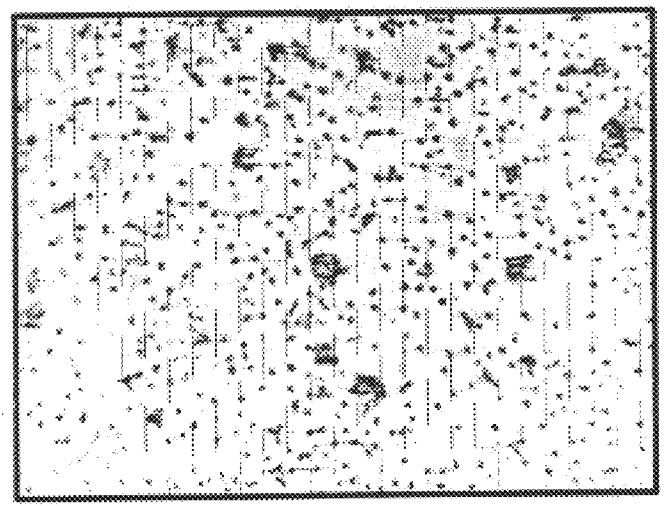
FIG. 8 is a photograph showing cells from a homotypic-adhesion assay wherein the cells were PDB-stimulated and treated with cLBE-R.

FIG. 6 illustrates that unstimulated cells in the homotypic-adhesion assay remained unclumped. FIG. 7 illustrates that cells treated with PDB only became clumped. FIG. 8 illustrates that PDB-stimulated cells treated cLBE-R were clumped to a lesser extent relative to cells treated with PDB alone, indicating that cLBE-R inhibited the binding of LFA-1 to ICAM-1.

Figure 9:
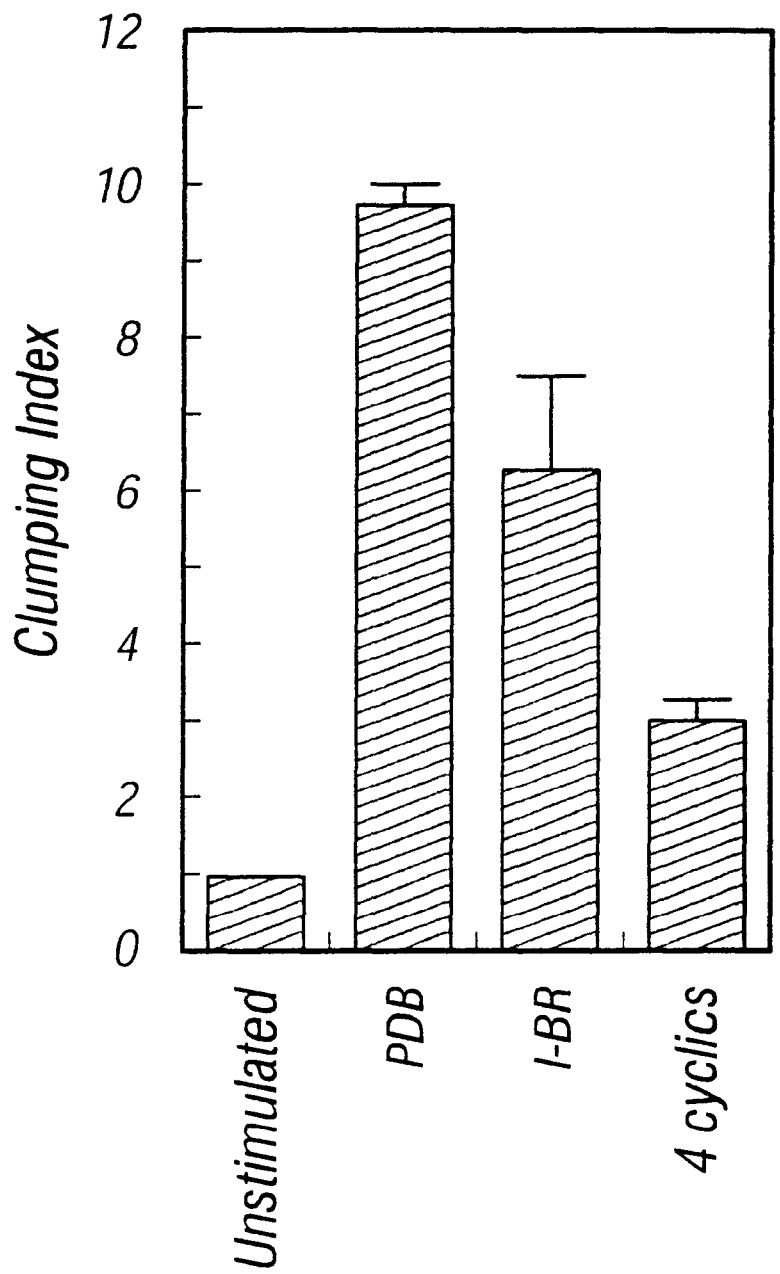
FIG. 9 is a bar graph illustrating the results of homotypic-adhesion assays wherein cells were unstimulated, PDB-stimulated, PDB-stimulated and treated with cIB-R, and PDB-stimulated and treated with a mixture of cIB-R, cLAB-L, cLAB.2-L, and cLBE-C (4 cyclics)
Figure 10:
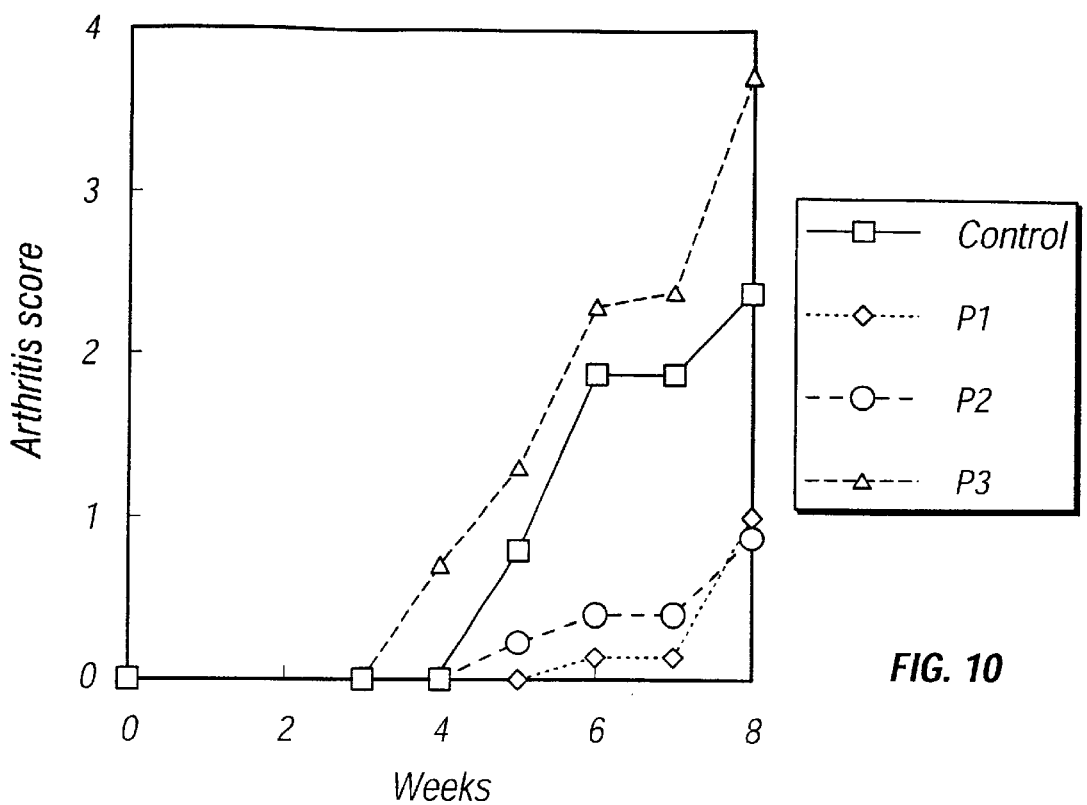
FIG. 10 is a graph illustrating the arthritis score test results generated during the induced arthritis mouse test described in Example 2.

FIG. 9 illustrates that a combination of cIB-R, cLAB-L, cLAB.2-L, and cLBE-C was much more effective than cIB-R alone in inhibiting PDB-stimulated cell clumping, indicating that this combination of peptides was more effective than cIB-R in inhibiting the binding of LFA-1 to ICAM-1. The results of homotypic-adhesion assays shown in FIG. 9 were represented using clumping-index values that ranged from 0 to 10 instead of using clumping-index values that ranged from 0 to 100 as shown in the table above. With respect to FIG. 9, a clumping-index value of 0 was obtained from the test run in which unstimulated cells showed the least amount of clumping. A clumping-index value of 100 was obtained from the test run in which PDB-stimulated cells showed the greatest amount of clumping. The clumping-index values for unstimulated cells and PDB-stimulated cells are not reported exactly as 0 and 10, respectively, because more than one test run was conducted using unstimulated cells and PDB-stimulated cells. Since the clumping-index values of 0 and 10 were based upon test runs giving the least amount and greatest amount of cell clumping, respectively, multiple test runs using unstimulated cells resulted in a mean clumping-index value greater than 0, and multiple test runs using PDB-stimulated cells resulted in a mean clumping index less than 10. As in the table above, clumping index was quantified by determining the mean clumping index per test run +/− standard error.

EXAMPLE 2

In this example, commercially available female DBA/1j mice (the Jackson Laboratory) were treated to induce arthritis and a number of the mice were dosed with peptides in accordance with the present invention.

The female mice were housed in an air conditioned room and quarantined for one week before use. The mice were given standard laboratory chow and tap water ad libitum. A control and three test groups (P1, P2 and P3) each consisted of ten mice.

Type II collagen (Sigma Chemical) was dissolved overnight in 0.05 N acetic acid at a concentration of 4 mg/ml, after which the solution was emulsified in an equal volume of complete Freund's adjuvant (Sigma Chemical). An aliquot of this emulsion containing 200 µg of Type II collagen was injected intradermally at the base of the tails of the test groups of mice. Twenty-one days later, an emulsion of Type II collagen and incomplete Freund's adjuvant (Sigma Chemical) containing 200 µg of the Type II collagen was injected intradermally.

The test groups were dosed with peptide mixtures suspended in normal saline intravenously once a day for five days after the first collagen injection, as follows:

P1: cIB-R (SEQ ID No. 7), 50 µg; cLBE-C (SEQ ID No. 34), 25 µg; cLAB.2-L (SEQ ID No. 26), 12.5 µg; and cLAB-L (SEQ ID No. 19), 12.5 µg.

P2: cIB-R (SEQ ID No. 7), 50 µg; cLBE-C (SEQ ID No. 34), 25 µg; and cLAB.2-L (SEQ ID No. 26), 25 µg.

P3: cIB-R (SEQ ID No. 7), 50 µg; cLBE-C (SEQ ID No. 34), 25 µg; and cLAB-L (SEQ ID No. 19), 25 µg.

The clinical symptoms of arthritis in all four limbs of the mice were evaluated using a visual scoring system. Arthritic lesion of a limb was graded on a scale of 0–3 (0=no change, 1=swelling and erythema of the digit, 2=mild swelling and erythema of the limb, 3=gross swelling and erythema of the limb). The arthritis score of each mouse was the sum of the score for each of the four limbs, the maximum score thus being 12. Arthritic incidence was also recorded. The incidence and arthritis score measurements were made over a period of five weeks, beginning at week 3 after initiation of the experiment.

Figure 11:
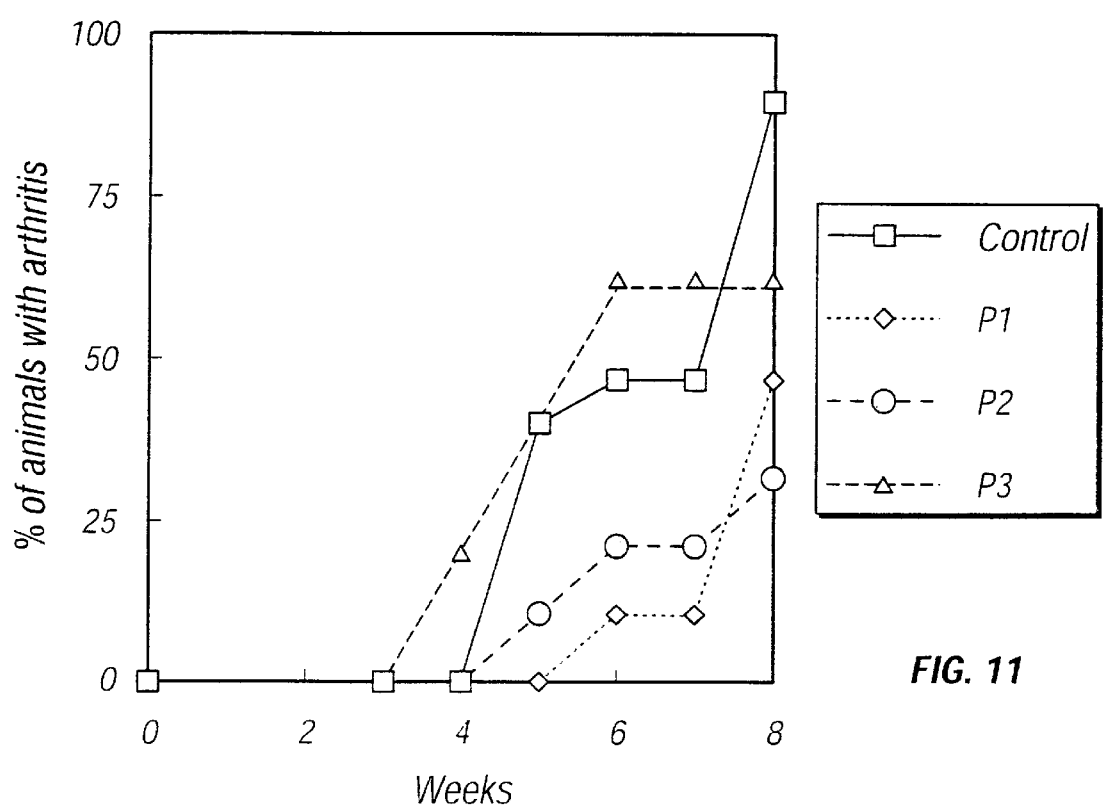
FIG. 11 is a graph depicting the arthritis incidence data generated during the induced arthritis mouse test described in Example 2.
Figure 12:
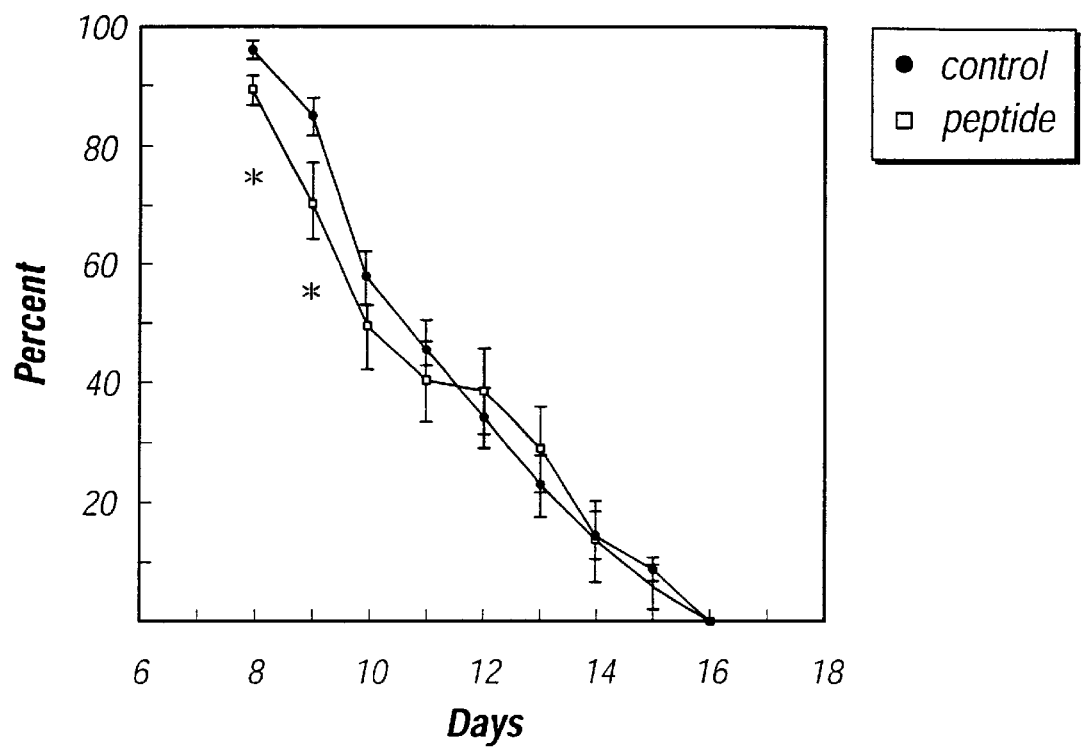
FIG. 12 is a graph illustrating the data developed during the mouse skin transplant test of Example 3.

Referring to FIGS. 11 and 12, it will be seen that 90% of the mice in the control group developed arthritis. The P1 and P2 groups showed inhibition of incidence, and the arthritis score was lower than the control between weeks 5–8. The P3 group exhibited an inhibition of incidence after the eighth week. However, the arthritis score of this group was higher than that of the control.

EXAMPLE 3

In this example, the effect of peptides in accordance with the invention on the rate of skin graft rejection in mice was studied. The technique was essentially as previously described (Rosenberg, 1991, Skin allograft rejection, In: Current Protocols in Immunology, Coico, R., Ed., Unit 4.4, Supplement 2, Current Protocols, the teachings of which are incorporated by reference herein).

In the first step, the donor skin tissue for the transplant was prepared. The entire tail was removed from a C3H (black) mouse. An incision was made on the dorsum of the tail down its entire length and the skin was peeled off. The skin was placed, internal surface down, on the bottom of a plastic petri dish containing enough TC-PBS to keep the tissue moist.

The recipient mice (1 control and 1 test BALB/c [white] mouse) were anesthetized with a ketamine/xylazine cocktail. A circumferential band was shaved around the thorax and abdomen from the shoulder joints to the hip joints of the mice. A 1 cm$^2$ graft bed was cut, and the skin was peeled off, leaving the panniculus carnosus intact. The graft tissue was then applied to each mouse, and the animals were then bandaged and held in separate housing for the duration of the study. 100 µl normal saline (control mouse) or 100 µl saline containing particles (test mouse) were administered i.p. (intraperitoneal) immediately prior to the surgery and once per day for four days following surgery. 175 µg each of cIB-R (SEQ ID No. 7). cLAB.2-L (SEQ ID No. 26), cLAB-L (SEQ ID No. 19), and cLBE-C (SEQ ID No. 34) were injected in a final volume of 100 µl normal saline in each peptide injection. The bandage was removed on day 7 following the operation and the grafts were graded daily by three separate people. A completely intact graft received a grade of 100%. A graft that had completely been rejected (scabbed over and fell off) was given a grade of 0%.

This test (FIG. 12) demonstrated that peptide treatment was able to significantly (p<005) delay the rejection of the skin graft for two days.

EXAMPLE 4

In this example, an MLR assay is performed using certain peptides in accordance with the invention, in order to demonstrate that the peptides inhibit the biological effectiveness of the involved T cells.

The one-way mixed lymphocyte reaction has been previously described (Kruisbeek et al., Current Protocols in Immunology, *Proliferative Assays for T Cell Function*, §3.12.1–3.12.14 (1991), incorporated by reference). Specifically, human tonsil T cells were suspended at a concentration of 4–10$^6$ cell/ml in cell culture medium (RPMI), for use as responders. Stimulator cells were human mononuclear cells isolated from first Ficoll separation of peripheral blood (buffy coat) and were suspended at a concentration of 4–10$^6$ cell/ml in RPMI culture medium. The stimulator cells were inactivated before use by treatment with 3,000 rad of ionizing radiation from $\gamma^{-137}$Cs source. 100 µl of each cell suspension were combined in each well of 96-well plate in the absence or presence of varying concentrations of test peptides, as detailed below. Cell proliferation was assessed after 72 hours, by $^3$H-thymidine addition to each well (1 µCi/well, 67 Ci/mmol) with incubation for six hours. The cells were harvested using a PHD Cell Harvester (Cambridge Technology, Inc., Watertown, Mass.); the incorporated $^3$H was assessed using a liquid scintillation counter (Packard Instrument, Inc., Donner's Grove, Ill.).

In FIGS. 13–17, Y-axis values are mean cpm±SE (counts per minute). PBL[rad] refers to irradiated buffy coat cells, and tonsil-T refers to T-lymphyocytes derived from tonsil. Mix refers to non-treated, mixed lymphocyte sample, which is the positive control (represented by dashed line). Inhibition of proliferation by anti-CD11 a antibody was used as a control for inhibition of the LFA-1:ICAM-1 interaction.

Figure 13:
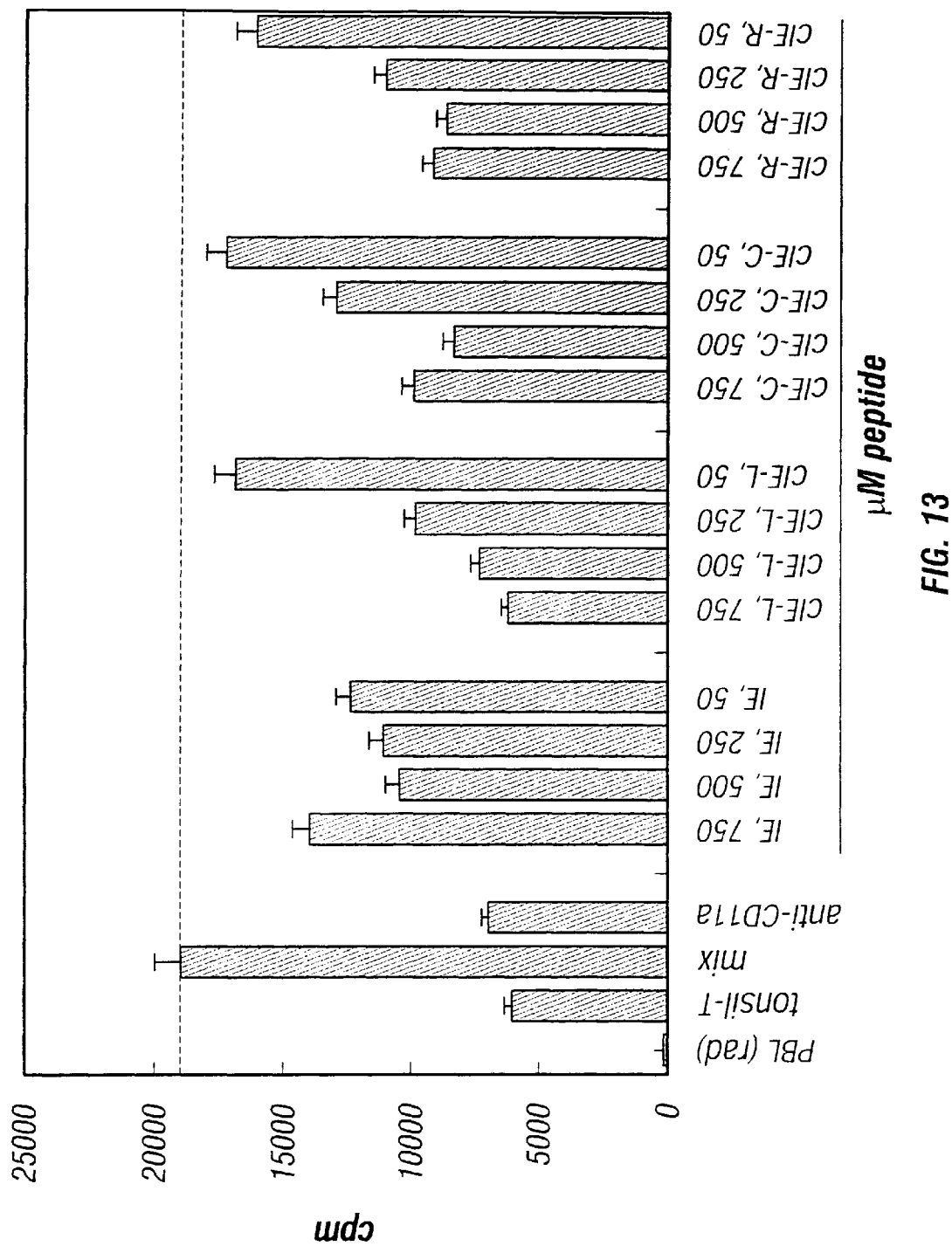
FIG. 13 is a bar graph illustrating the proliferation of responder cells in a mixed lymphocyte reaction assay, and the inhibitory effect of certain peptides in accordance with the invention on such proliferation.

Referring to FIG. 13, the MLR assay was performed in the presence or absence of IE peptide (SEQ ID No. 8) or cyclic fragments of IE (SEQ ID Nos. 8, 12, 13 and 14). Single peptides were tested at 250, 500, 750 and 1000 µM.

Figure 14:
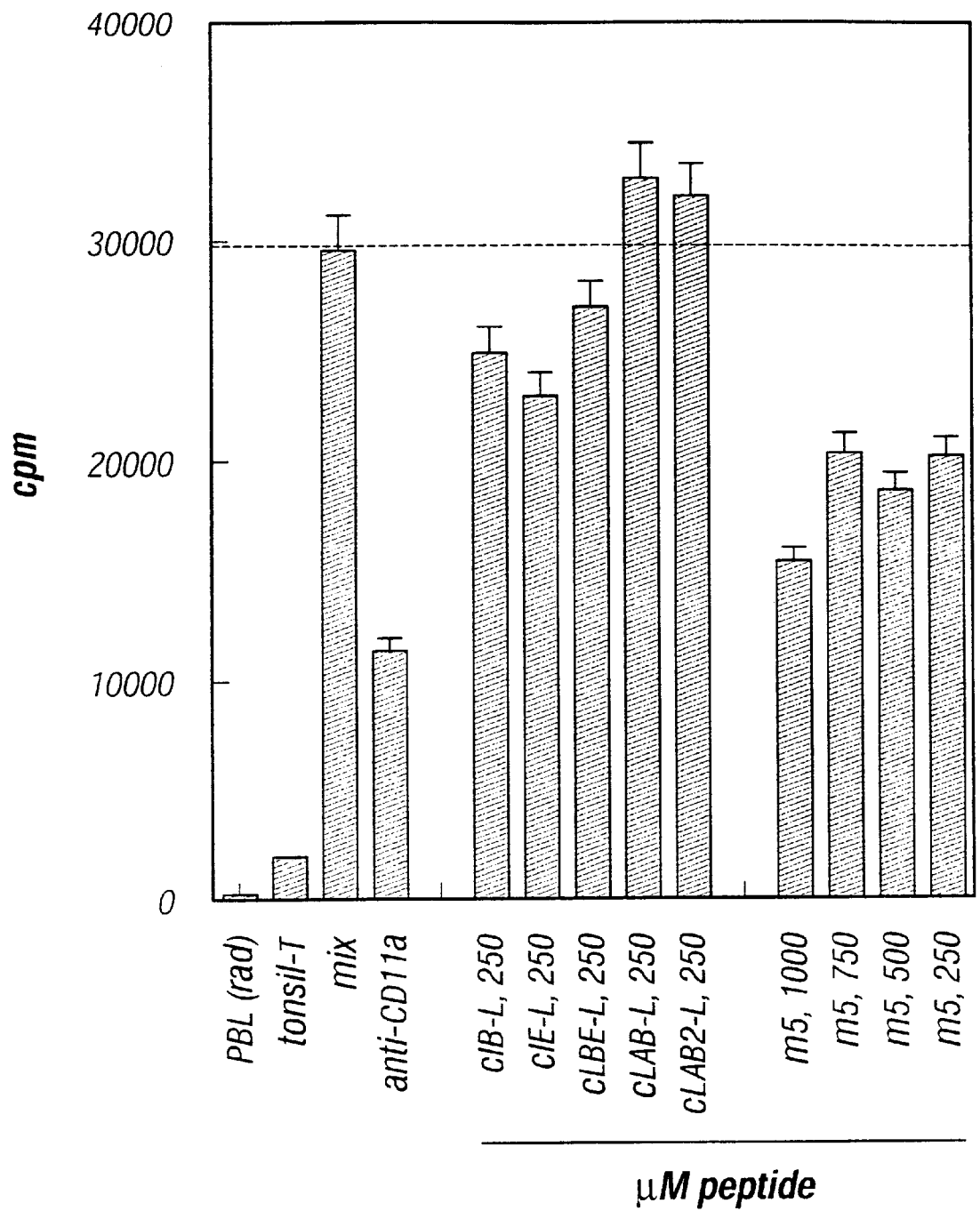
FIG. 14 is a bar graph illustrating the proliferation of responder cells in a mixed lymphocyte reaction assay, and the inhibitory effect of certain peptides in accordance with the invention on such proliferation.

As shown in FIG. 14, MLR was performed in the absence or presence of certain other peptides, namely cIB-L (SEQ ID No.5), cIE-L (SEQ ID No. 12), cLBE-L (SEQ ID No. 33), cLAB-L (SEQ ID No. 19), cLAB.2-L (SEQ ID No. 26) at 250 µM, and combinations of the five peptides (m5) at 250, 500, 750 and 1000 µM. The combination of the five peptides at 250 µM (cIB-L, CIE-L at 31.25 µM each and cLAB-L, cLAB.2-L and cLBE-L at 62.5 µM each) was more effective for inhibiting the proliferative response than any of the single peptides at 250 µM.

Figure 15:
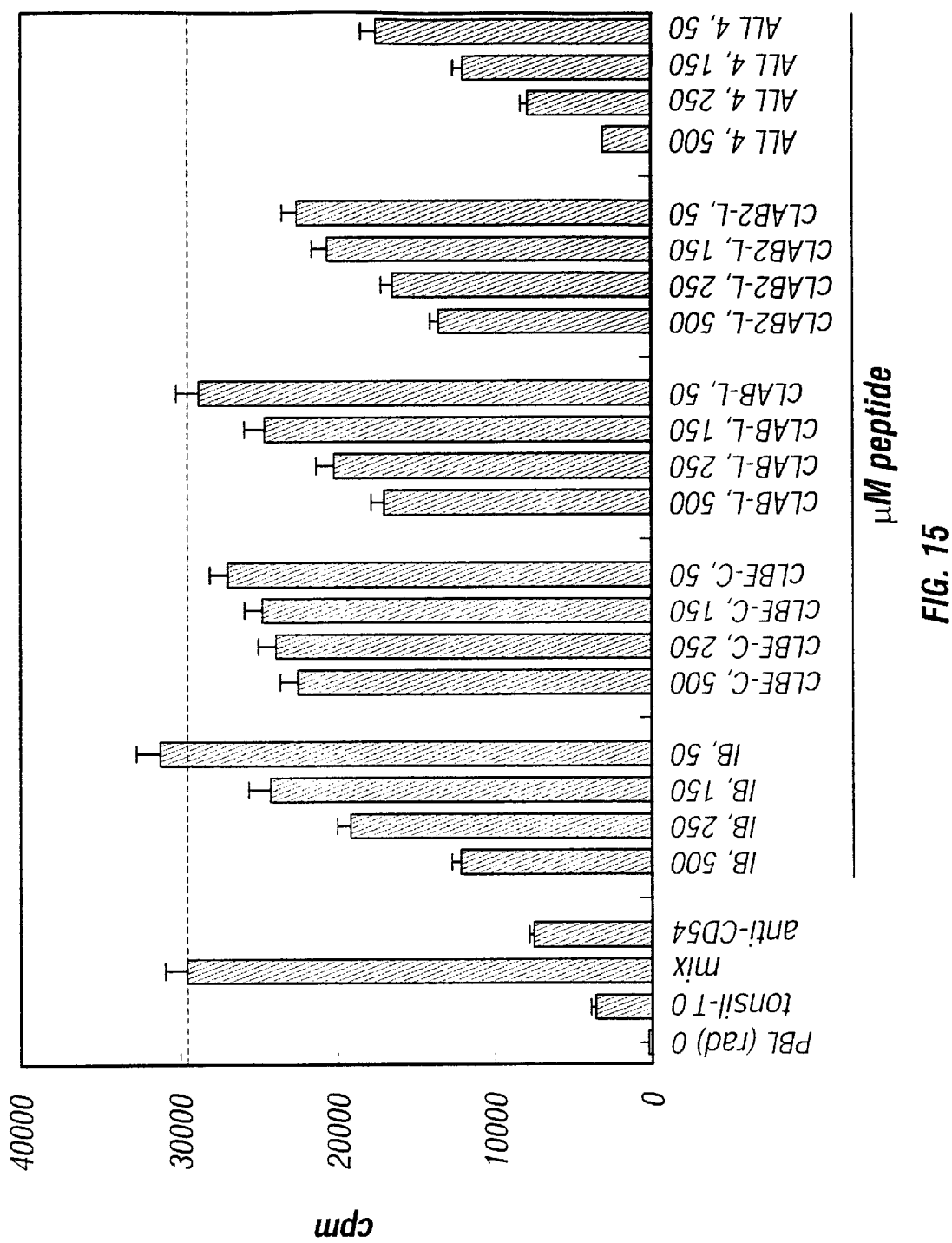
FIG. 15 is a bar graph illustrating the proliferation of responder cells in a mixed lymphocyte reaction assay, and the inhibitory effect of certain peptides in accordance with the invention on such proliferation.

FIG. 15 illustrates MLR assay results using single peptides tested at 50, 150, 250 and 500 µM (IB (SEQ ID No. 1), cLBE-C (SEQ ID No. 34), cLAB-L (SEQ ID No. 19) and cLAB.2-L (SEQ No. 26)), as well as combinations at the same concentration levels. The combined peptide treatment at each concentration was more effective in inhibiting the proliferative response than any of the single peptides at the same concentration.

Figure 16:
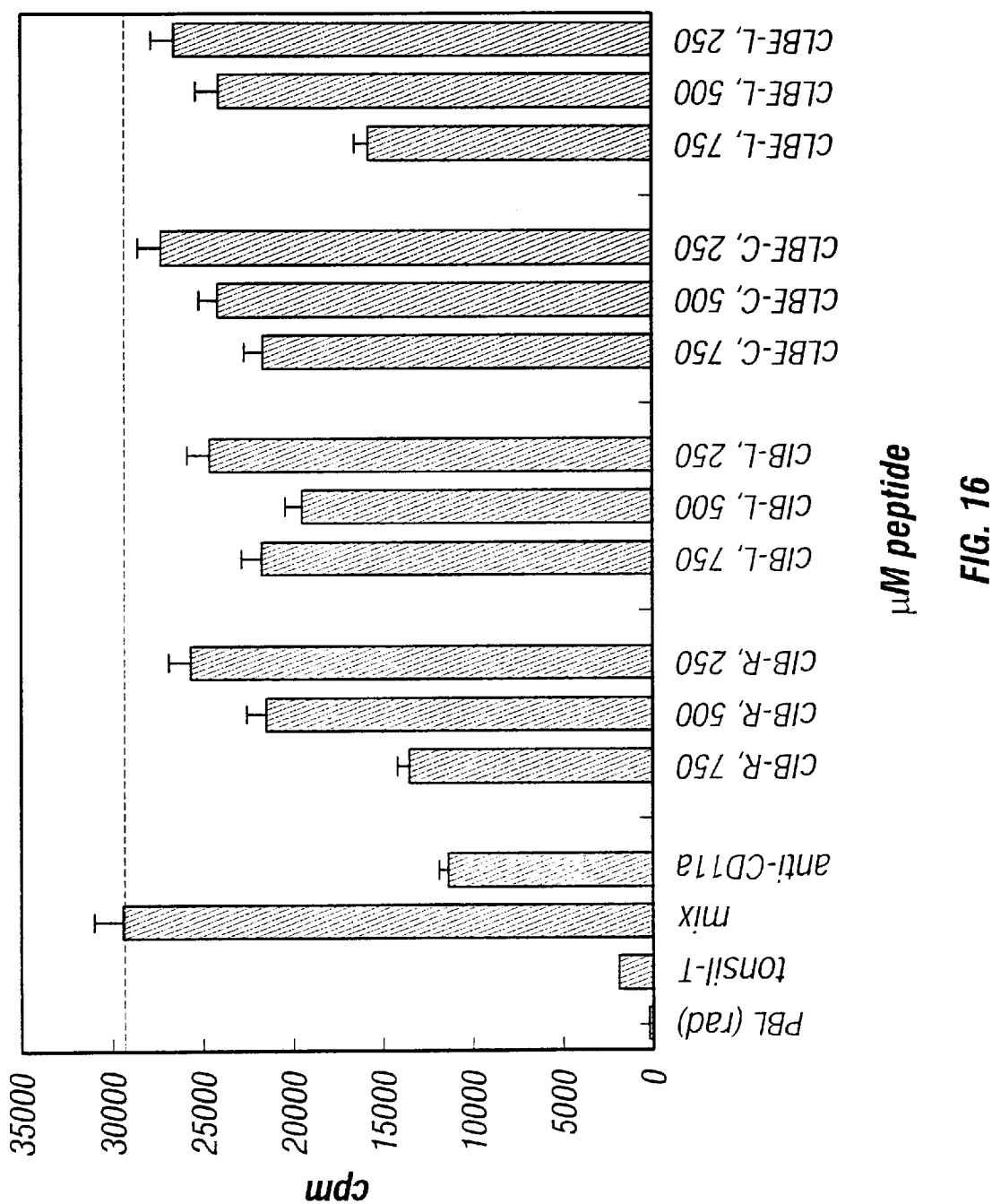
FIG. 16 is a bar graph illustrating the proliferation of responder cells in a mixed lymphocyte reaction assay, and the inhibitory effect of certain peptides in accordance with the invention on such proliferation.
Figure 17:
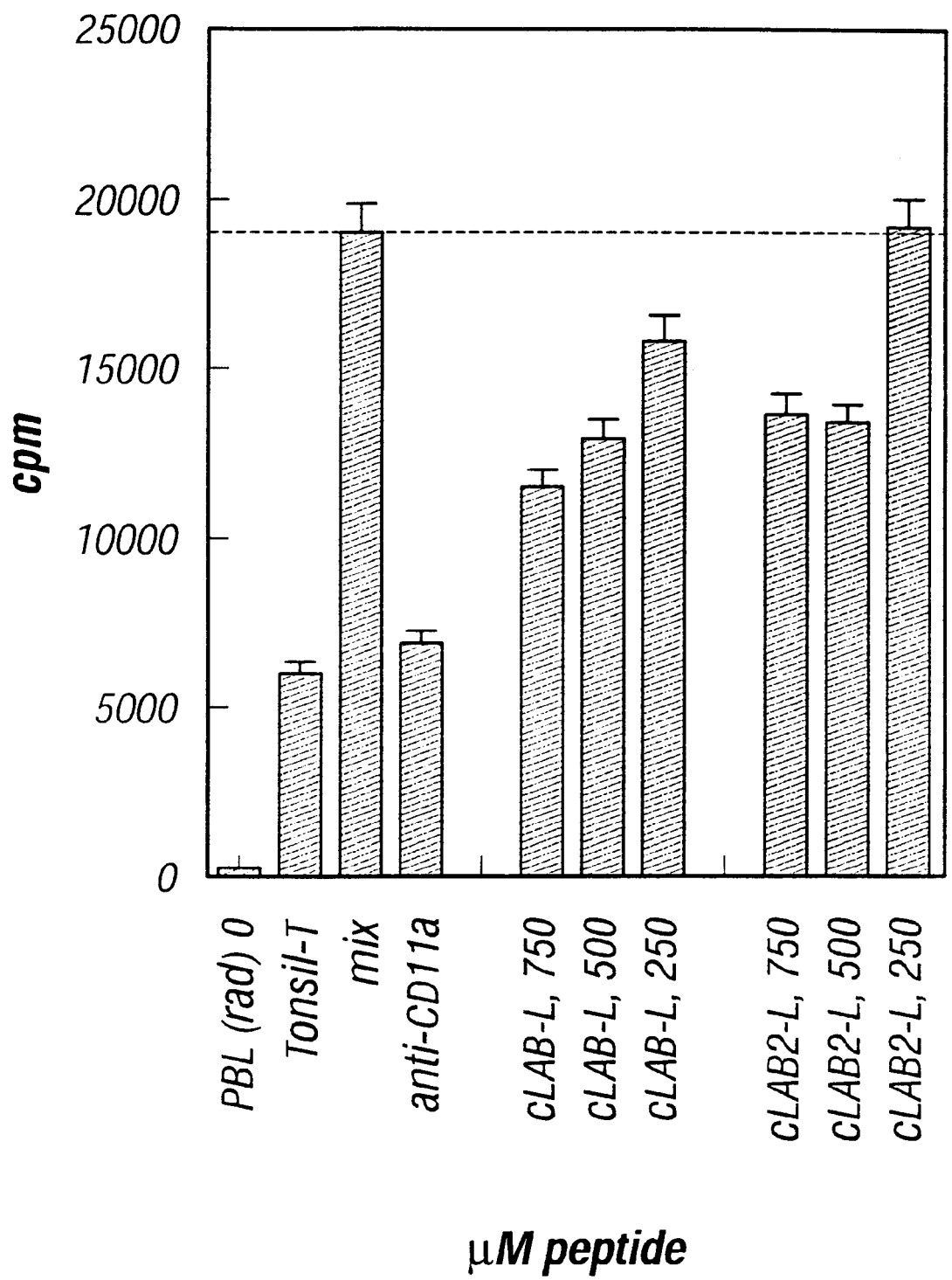
FIG. 17 is a bar graph illustrating the proliferation of responder cells in a mixed lymphocyte reaction assay, and the inhibitory effect of certain peptides in accordance with the invention on such proliferation.

FIGS. 16 and 17 illustrate an MLR wherein single peptides were tested at 250, 500 and 750 µM (cIB-R (SEQ ID No. 7), cIB-L (SEQ ID No. 5), cLBE-C (SEQ ID No. 34), cLBE-L (SEQ ID No. 33), cLAB-L (SEQ ID No. 19) and cLAB.2-L (SEQ ID No. 26)). These are cyclic fragments of the parent peptides IB and LBE (FIG. 16) and LAB and LAB.2 (FIG. 17). The above MLR assays demonstrate that the test peptides inhibited proliferation of the responder cells to a greater or lesser extent.

We claim:

1. A method of inhibiting the binding of LFA-1 to ICAM-1 comprising administering a peptide composition including at least two peptides, wherein at least one peptide comprises a sequence present in ICAM-1 and binds to LFA-1 and at least one peptide comprises a sequence present in α or β subunits of LFA-1 and binds to ICAM-1, whereby LFA-1 is inhibited from binding to ICAM-1.

2. The method of claim 1, wherein the binding is inhibited in an in vitro system or an organism.

3. The method of claim 2, wherein the organism is a mammal.

4. The method of claim 1, wherein the peptide that binds ICAM-1 comprises a sequence present in the α subunit of LFA-1.

5. The method of claim 4, wherein at least one of the peptides comprises a sequence selected from the group consisting of Sequences ID Nos. 1 through 14.

6. The method of claim 4, wherein at least one of the peptides comprises a sequence selected from the group consisting of Sequences ID Nos. 1 through 14.

7. The method of claim 4, wherein at least one of the peptides comprises a sequence present in a sequence selected from the group consisting of Sequences ID Nos. 15 through 35.

8. The method of claim 4, wherein at least one of the peptides comprises a sequence selected from the group consisting of Sequences ID Nos. 15 through 35.

9. The method of claim 4, wherein the composition comprises peptides having the sequences of sequence ID Nos. 7, 19, 26, and 34.

10. The method of claim 1, wherein at least one of the peptides is not immunogenic.

11. The method of claim 1, wherein at least one of the peptides has a molecular weight under 20 kilodaltons.

12. The method of claim 1, wherein at least one of the peptides contains at least one unnatural amino acid.

13. The method of claim 1, wherein at least one of the peptides is cyclic.

14. The method of claim 1, wherein at least one of the peptides is not covalently attached to another peptide.

15. The method of claim 1, wherein the method is effective in treating a disease state.

16. The method of claim 15, wherein the disease state is selected from the group consisting of rejection of a transplanted organ, an allergy, and an autoimmune disease.

17. The method of claim 16, wherein the autoimmune disease is selected from the group consisting of rheumatoid arthritis, insulin-dependent diabetes mellitus, and multiple sclerosis

UNITED STATES PATENT AND TRADEMARK OFFICE
CERTIFICATE OF CORRECTION

PATENT NO.    : 6,653,282 B1
DATED         : November 25, 2003
INVENTOR(S)   : Stephen H. Benedict et al.

It is certified that error appears in the above-identified patent and that said Letters Patent is hereby corrected as shown below:

<u>Title page,</u>
Item [76], Inventors, please change "Siaiiann" to -- Siahaan --

Signed and Sealed this

Third Day of February, 2004

JON W. DUDAS
*Acting Director of the United States Patent and Trademark Office*

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 21 amino acids
      (B) TYPE: amino acid
      (D) TOPOLOGY: linear (ii) MOLECULE TYPE: peptide (xi) SEQUENCE DESCRIPTION: SEQ ID NO: 1:

Gln Thr Ser Val Ser Pro Ser Lys Val Ile Leu Pro Arg Gly Gly Se
1          5                  10                15

Val Leu Val Thr Gly
        20

(2) INFORMATION FOR SEQ ID NO: 2:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 2:

```
Xaa Gln Thr Ser Val Ser Pro Ser Lys Val Ile Cys
1               5                   10
```

(2) INFORMATION FOR SEQ ID NO: 3:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 3:

```
Xaa Pro Ser Lys Val Ile Leu Pro Arg Gly Gly Cys
1               5                   10
```

(2) INFORMATION FOR SEQ ID NO: 4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 4:

```
Cys Leu Pro Arg Gly Gly Ser Val Leu Val Thr Cys
1               5                   10
```

(2) INFORMATION FOR SEQ ID NO: 5:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 5:

```
Xaa Gln Thr Ser Val Ser Pro Ser Lys Val Ile Cys
1               5                   10
```

(2) INFORMATION FOR SEQ ID NO: 6:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 6:

```
Xaa Pro Ser Lys Val Ile Leu Pro Arg Gly Gly Cys
1               5                   10
```

(2) INFORMATION FOR SEQ ID NO: 7:

(i) SEQUENCE CHARACTERISTICS:

(A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 7:

Cys Leu Pro Arg Gly Gly Ser Val Leu Val Thr Cys
1               5                   10

(2) INFORMATION FOR SEQ ID NO: 8:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 8:

Asp Gln Pro Lys Leu Leu Gly Ile Glu Thr Pro Leu Pro Lys Lys Gl
1               5                   10                  15

Leu Leu Leu Pro Gly Asn Asn Arg Lys
            20                  25

(2) INFORMATION FOR SEQ ID NO: 9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 9:

Xaa Asp Gln Pro Lys Leu Leu Gly Ile Glu Thr Cys
1               5                   10

(2) INFORMATION FOR SEQ ID NO: 10:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 10:

Xaa Glu Thr Pro Leu Pro Lys Lys Glu Leu Leu Cys
1               5                   10

(2) INFORMATION FOR SEQ ID NO: 11:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 11:

Xaa Glu Leu Leu Leu Pro Gly Asn Asn Arg Lys Cys
1               5                   10

(2) INFORMATION FOR SEQ ID NO: 12:

(i) SEQUENCE CHARACTERISTICS:
        (A) LENGTH: 12 amino acids (B) TYPE: amino acid
(D) TOPOLOGY: circular (ii) MOLECULE TYPE: peptide (xi) SEQUENCE DESCRIPTION: SEQ ID NO: 12:

```
Xaa Asp Gln Pro Lys Leu Leu Gly Ile Glu Thr Cys
1               5                   10
```

(2) INFORMATION FOR SEQ ID NO: 13:

(i) SEQUENCE CHARACTERISTICS:
      (A) LENGTH: 12 amino acids
      (B) TYPE: amino acid
      (D) TOPOLOGY: circular (ii) MOLECULE TYPE: peptide (xi) SEQUENCE DESCRIPTION: SEQ ID NO: 13:

```
Xaa Glu Thr Pro Leu Pro Lys Lys Glu Leu Leu Cys
1               5                   10
```

(2) INFORMATION FOR SEQ ID NO: 14:

(i) SEQUENCE CHARACTERISTICS:
      (A) LENGTH: 12 amino acids
      (B) TYPE: amino acid
      (D) TOPOLOGY: circular (ii) MOLECULE TYPE: peptide (xi) SEQUENCE DESCRIPTION: SEQ ID NO: 14:

```
Xaa Glu Leu Leu Leu Pro Gly Asn Asn Arg Lys Cys
1               5                   10
```

(2) INFORMATION FOR SEQ ID NO: 15:

(i) SEQUENCE CHARACTERISTICS:
      (A) LENGTH: 24 amino acids
      (B) TYPE: amino acid
      (D) TOPOLOGY: linear (ii) MOLECULE TYPE: peptide (xi) SEQUENCE DESCRIPTION: SEQ ID NO: 15:

```
Ile Thr Asp Gly Glu Ala Thr Asp Ser Gly Asn Ile Asp Ala Ala Ly
1               5                   10                  15
Asp Ile Ile Tyr Ile Ile Gly Ile
                20
```

(2) INFORMATION FOR SEQ ID NO: 16:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (xi) SEQUENCE DESCRIPTION: SEQ ID NO: 16:

```
Xaa Ile Thr Asp Gly Glu Ala Thr Asp Ser Gly Cys
1               5                   10
```

(2) INFORMATION FOR SEQ ID NO: 17:

(i) SEQUENCE CHARACTERISTICS:
      (A) LENGTH: 12 amino acids
      (B) TYPE: amino acid

```
            (D) TOPOLOGY: linear (ii) MOLECULE TYPE: peptide (xi) SEQUENCE DESCRIPTION: SEQ ID NO: 17:

Xaa Asp Ser Gly Asn Ile Asp Ala Ala Lys Asp Cys
1               5                   10

(2) INFORMATION FOR SEQ ID NO: 18:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 18:

Xaa Ala Lys Asp Ile Ile Tyr Ile Ile Gly Ile Cys
1               5                   10

(2) INFORMATION FOR SEQ ID NO: 19:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 19:

Xaa Ile Thr Asp Gly Glu Ala Thr Asp Ser Gly Cys
1               5                   10

(2) INFORMATION FOR SEQ ID NO: 20:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 20:

Xaa Asp Ser Gly Asn Ile Asp Ala Ala Lys Asp Cys
1               5                   10

(2) INFORMATION FOR SEQ ID NO: 21:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 21:

Xaa Ala Lys Asp Ile Ile Tyr Ile Ile Gly Ile Cys
1               5                   10

(2) INFORMATION FOR SEQ ID NO: 22:

(i) SEQUENCE CHARACTERISTICS:
        (A) LENGTH: 24 amino acids
        (B) TYPE: amino acid
        (D) TOPOLOGY: linear (ii) MOLECULE TYPE: peptide
```

(xi) SEQUENCE DESCRIPTION: SEQ ID NO: 22:

Gly Val Asp Val Asp Gln Asp Gly Glu Thr Glu Leu Ile Gly Ala Pr
1               5                   10                  15

Leu Phe Tyr Gly Glu Gln Arg Gly
            20

(2) INFORMATION FOR SEQ ID NO: 23:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 23:

Xaa Gly Val Asp Val Asp Gln Asp Gly Glu Thr Cys
1               5                   10

(2) INFORMATION FOR SEQ ID NO: 24:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 24:

Xaa Gly Glu Thr Glu Leu Ile Gly Ala Pro Leu Cys
1               5                   10

(2) INFORMATION FOR SEQ ID NO: 25:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 25:

Xaa Ala Pro Leu Phe Tyr Gly Glu Gln Arg Gly Cys
1               5                   10

(2) INFORMATION FOR SEQ ID NO: 26:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 26:

Xaa Gly Val Asp Val Asp Gln Asp Gly Glu Thr Cys
1               5                   10

(2) INFORMATION FOR SEQ ID NO: 27:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 27:

```
Xaa Gly Glu Thr Glu Leu Ile Gly Ala Pro Leu Cys
1               5                   10
```

(2) INFORMATION FOR SEQ ID NO: 28:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 28:

```
Xaa Ala Pro Leu Phe Tyr Gly Glu Gln Arg Gly Cys
1               5                   10
```

(2) INFORMATION FOR SEQ ID NO: 29:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 29:

```
Asp Leu Ser Tyr Ser Leu Asp Asp Leu Arg Asn Val Lys Lys Leu Gl
1               5                   10                  15
Gly Asp Leu Leu Arg Ala Leu Asn Glu
                20                  25
```

(2) INFORMATION FOR SEQ ID NO: 30:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 30:

```
Xaa Asp Leu Ser Tyr Ser Leu Asp Asp Leu Arg Cys
1               5                   10
```

(2) INFORMATION FOR SEQ ID NO: 31:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 31:

```
Xaa Asp Leu Arg Asn Val Lys Lys Leu Gly Gly Cys
1               5                   10
```

(2) INFORMATION FOR SEQ ID NO: 32:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 32:

```
Xaa Gly Gly Leu Leu Arg Ala Leu Asn Glu Cys
1               5                   10
```

(2) INFORMATION FOR SEQ ID NO: 33:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 33:

```
Xaa Asp Leu Ser Tyr Ser Leu Asp Asp Leu Arg Cys
1               5                   10
```

(2) INFORMATION FOR SEQ ID NO: 34:

(i) SEQUENCE CHARACTERISTICS:
        (A) LENGTH: 12 amino acids
        (B) TYPE: amino acid
        (D) TOPOLOGY: circular (ii) MOLECULE TYPE: peptide (xi) SEQUENCE DESCRIPTION: SEQ ID NO: 34:

```
Xaa Asp Leu Arg Asn Val Lys Lys Leu Gly Gly Cys
1               5                   10
```

(2) INFORMATION FOR SEQ ID NO: 35:

(i) SEQUENCE CHARACTERISTICS:
        (A) LENGTH: 11 amino acids
        (B) TYPE: amino acid
        (D) TOPOLOGY: circular (ii) MOLECULE TYPE: peptide (xi) SEQUENCE DESCRIPTION: SEQ ID NO: 35:

```
Xaa Gly Gly Leu Leu Arg Ala Leu Asn Glu Cys
1               5                   10
```

(2) INFORMATION FOR SEQ ID NO: 36:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 36:

```
Glu Asn Leu Ala Arg Leu Leu Asp Gly Gly Leu Lys Lys Val Asn Ar
1               5                   10                  15
Leu Asp Asp Leu Ser Tyr Ser Leu Asp
                20                  25
```